(12) United States Patent
Essenreiter et al.

(10) Patent No.: US 10,028,790 B2
(45) Date of Patent: Jul. 24, 2018

(54) WRONG LEVEL SURGERY PREVENTION

(71) Applicant: Brainlab AG, Munich (DE)

(72) Inventors: Robert Essenreiter, Munich (DE); Manfred Weiser, Munich (DE)

(73) Assignee: Brainlab AG, Munich (DE)

( * ) Notice: Subject to any disclaimer, the term of this patent is extended or adjusted under 35 U.S.C. 154(b) by 292 days.

(21) Appl. No.: 14/895,552

(22) PCT Filed: Jul. 19, 2013

(86) PCT No.: PCT/EP2013/065268
§ 371 (c)(1),
(2) Date: Dec. 3, 2015

(87) PCT Pub. No.: WO2015/007333
PCT Pub. Date: Jan. 22, 2015

(65) Prior Publication Data
US 2016/0120608 A1    May 5, 2016

(51) Int. Cl.
*A61B 5/00*     (2006.01)
*A61B 34/20*    (2016.01)
*A61B 90/00*    (2016.01)

(52) U.S. Cl.
CPC ............ *A61B 34/20* (2016.02); *A61B 90/37* (2016.02); *A61B 2034/2055* (2016.02);
(Continued)

(58) Field of Classification Search
CPC . A61B 34/20; A61B 90/37; A61B 2034/2068; A61B 2090/3762; A61B 2090/374; A61B 2034/2055
See application file for complete search history.

(56) References Cited

U.S. PATENT DOCUMENTS

2006/0050942 A1   3/2006  Bertram
2006/0084867 A1*  4/2006  Tremblay ............... A61B 90/36
                                                    600/434
(Continued)

FOREIGN PATENT DOCUMENTS

EP          2017785        1/2009

OTHER PUBLICATIONS

PCT/EP2013/065268—International Search Report dated Jun. 25, 2014.
(Continued)

*Primary Examiner* — Joel Lamprecht
(74) *Attorney, Agent, or Firm* — Tucker Ellis LLP

(57) ABSTRACT

The invention relates to a method of relating a position (pos(selected)) of an anatomical structure (3) and a position of an image feature representing the anatomical structure in a medical image (11), the method being constituted to be executed by a computer and comprising: a) acquiring information about the position of a medical imaging apparatus (1) at the beginning (pos(start)) and at the end (pos(end)) of acquiring medical image information describing a medical image (11) of at least a part of a patient's body (2) comprising the anatomical structure (3), wherein the medical imaging apparatus (1) is moved while it is used for acquiring the medical image information; b) acquiring imaging information about a relationship between the movement of the medical imaging apparatus and the acquisition of the medical image information; c) acquiring, based on the position of the medical imaging apparatus at the beginning (pos(start)) and at the end (pos(end)) of acquiring the medical image information, information about a predominant direction of movement (z) of the medical imaging apparatus (1); d) acquiring information about the position of a pointer means (12) in the predominant direction of movement (z); e)

(Continued)

determining, based on the information about the position of the medical imaging apparatus (1) at the beginning (pos (start)) and at the end (pos(end)) of acquiring the medical image information and based on the information about the position of the pointer means (12) and based on the imaging information, information about a transformation between the position in the medical image (11) of an image feature representing the anatomical structure (3) and the position of the anatomical structure (3) in a navigation reference system (17).

16 Claims, 1 Drawing Sheet

(52) U.S. Cl.
CPC . *A61B 2034/2068* (2016.02); *A61B 2090/374* (2016.02); *A61B 2090/3762* (2016.02)

(56) References Cited

U.S. PATENT DOCUMENTS

| | | | |
|---|---|---|---|
| 2010/0210939 A1* | 8/2010 | Hartmann | A61B 5/062 600/424 |
| 2010/0228117 A1 | 9/2010 | Hartmann | |
| 2012/0289826 A1 | 11/2012 | Graumann et al. | |

OTHER PUBLICATIONS

Cheerag D. Upadhyaya, M.D., et al. Avoidance of wrong-level thoracic spine surgery: intraoperative localization with preoperative percutaneous fiducial screw placement; Clinical article; J. Neurosurg Spine 16:280-284—2012; vol. 16; Mar. 2012.

\* cited by examiner

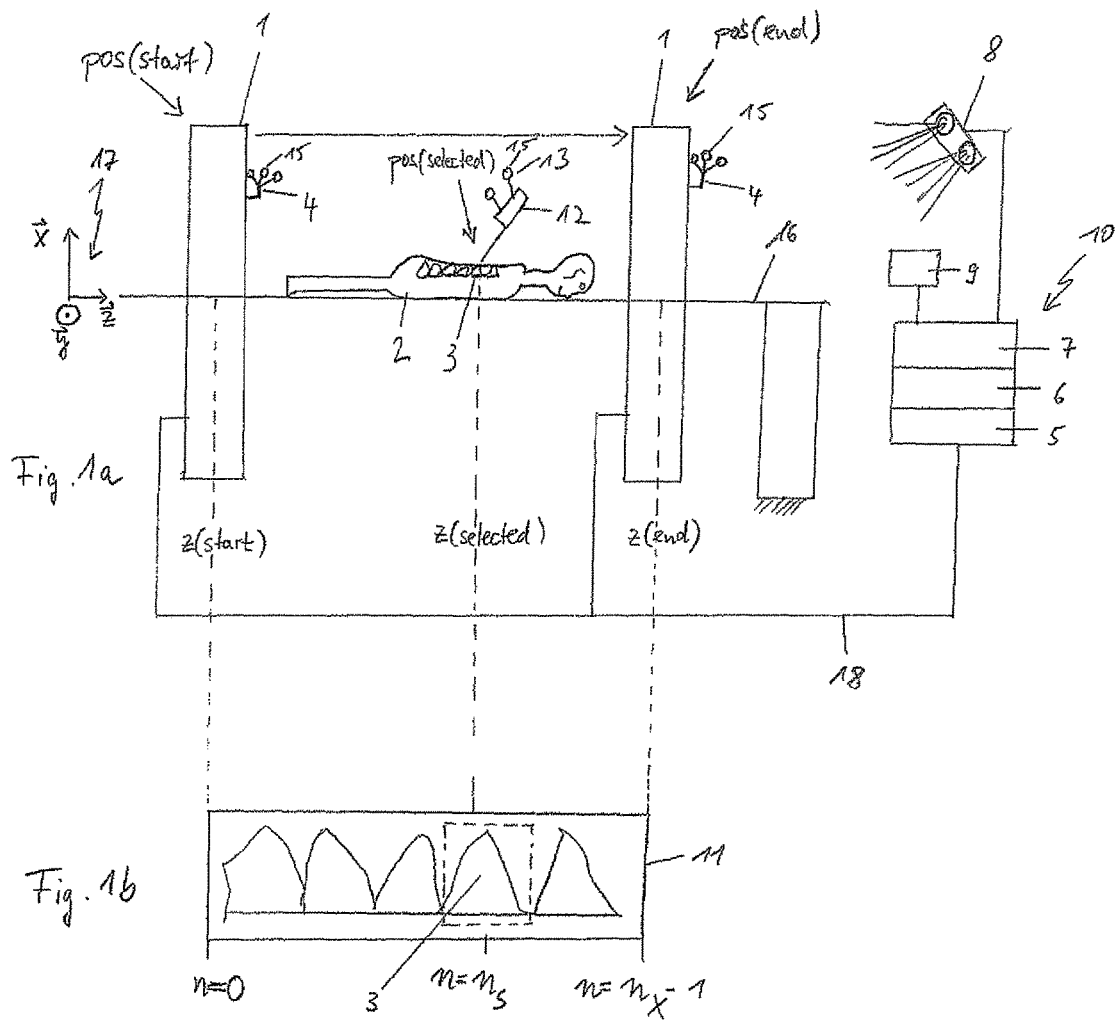

WRONG LEVEL SURGERY PREVENTION

RELATED APPLICATION DATA

This application is a national phase application of International Application No. PCT/EP2013/065268 filed Jul. 19, 2013, published in the English language.

The invention relates to the general technical field of relating a position of an anatomical structure and a position of an image feature representing the anatomical structure in a medical image.

In medical procedures such as image-guided surgery (IGS) or radiotherapy, it is desirable to know the position of a specific anatomical structure in a medical image of the body of a patient who is to be treated. For example, medical personnel wishes to associate a visually identified part of the real body with a specific image feature representing that part of the real body in order to determine a location on the specific patient's body at which the envisaged medical procedure is to be carried out.

For example, a medical procedure shall be carried out on the patient's spine and medical personnel manually detects a specific vertebra in the patient's body. The position of the specific vertebra shall then be determined in a medical image, for example an X-ray image, taken of the patient's body (including the spine). A known approach to determine such information of the position of the vertebra in the image includes placing a radioopaque structure on the patient's body in the imaging direction of the X-ray apparatus between the X-ray source and the vertebra and to count the patient's real vertebrae outgoing from the position of the radioopaque structure in both the patient environment and the medical image, and then comparing the counting result with the vertebrae depicted in the image. Thereby, the position of specific vertebrae which have not themselves been directly marked with the radioopaque structure may be determined in the image. Instead of a radioopaque structure, an anatomical landmark such as an easily recognizable specific vertebra may be used as a positional reference.

This known approach, however, may lead to wrong results in determining the position of the vertebra in the image due to for example a counting error by the medical personnel. Furthermore, this approach is cumbersome and potentially associated with applying a high radiation dose to both medical personnel and patient. A problem to be solved by the invention therefore is to provide an efficient and reliable method of determining the position of an anatomical structure in a medical image.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature. A feature of one embodiment which adds an additional function to another embodiment can in particular be added to said other embodiment.

EXEMPLARY SHORT DESCRIPTION OF THE PRESENT INVENTION

In the following, a concise description of the present invention is offered which is to be considered merely as an example and not as a limitation of the invention to the features described in this section.

The present invention provides in particular a method of relating (i.e. determining a relationship between) the position of an anatomical structure (in particular a bony structure such as a vertebra or a rib) and the position of an image feature representing the anatomical structure in a medical image, which method includes tracking the position of a medical imaging apparatus such as the gantry of a CT scanner while it moves during acquisition of the medical image. This position is preferably determined by tracking, with a medical navigation system, markers having a preferably fixed position relative to the medical imaging apparatus. Based on the results of the tracking, a predominant direction of movement of the medical imaging apparatus is determined. A relationship between the movement of the medical imaging apparatus and the acquisition of the medical image is known for example as a relationship between the velocity of the medical imaging apparatus and its imaging frequency. Then, a pointer means is used to identify the position of the anatomical structure in particular along the predominant direction of movement, and the position of the pointer is also determined by the navigation system for example by tracking a marker device having a fixed spatial relationship relative to the pointer. A position in the medical image information is then determined which corresponds to the position which is identified by the pointer means. The user is then supplied with information indicating to him the image feature in the medical image which corresponds to the anatomical structure.

The invention also provides a computer program which comprises code for executing the aforementioned method, a computer running that program and a navigation system which comprises in particular the aforementioned computer.

GENERAL DESCRIPTION OF THE INVENTION

In this section a general description of the features and embodiment of the present invention is offered. The features described in the following constitute preferred and particular features of the invention.

Preferably, information about the position of a medical imaging apparatus is acquired at the beginning and at the end of a acquiring medical image information describing a medical image of at least a part of a patient's body. The part of the patient's body comprises an anatomical structure and the medical imaging apparatus is moved while it is used for acquiring the medical image information. In a further preferred embodiment, the invention comprises a step of issuing control information to the medical imaging apparatus (in particular to a driving unit operatively coupled to the medical imaging apparatus) to make it move. However, the inventive method does not necessarily comprise a step of moving the medical imaging apparatus and/or issuing such control data.

As a medical imaging apparatus, for example an X-ray source such as a CT scanner or a single X-ray tube is used. Alternatively, the medical imaging apparatus may comprise a radiation source for magnetic resonance tomography (MRT), in particular, the medical imaging apparatus may constitute a magnetic resonance tomograph. Preferably at least part of the medical imaging apparatus is movable. In the case of a CT scanner or a magnetic resonance tomograph, the movable part of the medical imaging apparatus comprises, in particular consists of, for example the gantry of the CT or MR scanner. Preferably, tracking information about the position of the medical imaging apparatus is acquired. For example, the position of the medical imaging apparatus is tracked in particular while the medical imaging apparatus acquires medical image information (in particular over the entire length of time of acquiring the medical image data). The medical image information is acquired in particular during movement of the medical imaging apparatus and describes in particular a medical image of at least a part of a patient's body comprising an anatomical structure which is in particular of interest to the user and/or an envisaged medical procedure. The position of the medical imaging apparatus is tracked preferably by detecting a marker device having a predetermined spatial relationship to the medical imaging apparatus. The marker device comprises in particular at least one retroreflective marker, more particularly three retroreflective markers. The marker device is preferably attached to the medical imaging apparatus, for example to the gantry of a CT scanner or an MR scanner and is detected by the detection unit of a medical navigation system. The detection unit is for example a stereotactic camera which works for example on the principle of detecting infrared radiation reflected from a retroreflective marker. A spatial relationship, in particular at least one of position and orientation of the marker device relative to the medical imaging apparatus (in particular relative to the gantry) is predetermined, i.e. known to the method, and further preferably fixed, i.e. does not change at least during execution of the inventive method.

Alternatively, the position of the medical imaging apparatus may be tracked by for example electromechanic and/or analog-to-digital conversion of movement signals received from a positioning and moving unit operatively coupled to the movable part of the medical imaging apparatus in order to move it. For example, position detectors may be included in a rail which serves to guide the movement of the movable part of the medical imaging apparatus. The corresponding position signals may be read by the computer of the navigation system and converted into positions in the navigation coordinate system in particular based on information of at least one position of the movable part of the medical imaging apparatus as a reference position (e.g. based on information about the start position of the medical imaging apparatus) in the navigation coordinate system.

Preferably, the information about the position of the medical imaging apparatus is acquired at the beginning and the end of acquiring the medical image information. In particular, acquisition of the medical image information starts at the same point in time at which tracking the position of the medical imaging apparatus while moving it for acquisition of the medical image information starts. Further particularly, the position of the medical imaging apparatus is acquired at (in particular exactly) the points in time at which movement of the medical imaging apparatus during acquisition of the medical image information stops and at which acquisition of the medical image information is ended. Further preferably, the position of the medical imaging apparatus is tracked during the whole time during which the medical imaging apparatus acquires medical image information.

On that basis, preferably imaging information about a relationship between the movement (in particular the position) of the medical imaging apparatus and the acquisition of the medical image information is determined or acquired by the inventive method. In particular, a relationship between the imaging frequency and the moving velocity of the medical imaging apparatus is predetermined and known to the inventive method. The moving velocity is in particular the moving velocity in a predominant direction of movement of the medical imaging apparatus. On that basis and further based on time information, a position of the medical imaging apparatus on in particular a straight line in the predominant direction of movement can be determined. Thereby, for example a relationship between a set of medical image information (e.g. a single medical image) and the position which the medical imaging apparatus had when it acquired that set of medical image information is preferably predetermined and information about this relationship is acquired by the inventive method. According to a specific embodiment, the information about this relationship may be determined on-line, i.e. while the medical imaging apparatus is acquiring the medical image information, from e.g. the measured actual velocity and actual imaging frequency of the medical imaging apparatus. The velocity may be determined (in particular measured) e.g. based on positional and time information acquired in connection with (in particular by) tracking the medical imaging apparatus. Then it is preferred that at least the imaging frequency is known the inventive method, i.e. that the imaging frequency is predetermined or determined during image acquisition. The time information which may be required to establish the imaging information is preferably determined based on timing signals which are determined when acquisition of the medical image information is started and stopped, respectively.

At least part of the medical imaging apparatus is movable which means in particular that at least part of the medical imaging apparatus does not rest relative to a coordinate system in which the spatial relationships (i.e. positions and orientations) acquired and determined during execution of the inventive method are defined (which is also called a navigation coordinate system). Such a navigation coordinate system may rest for example in the position of the detection unit, in particular in the position of the camera used for detecting the marker devices.

Preferably, information about a predominant direction (also termed preferred direction) of movement of the medical imaging apparatus is acquired based on the information about the position of the medical imaging apparatus at the beginning and at the end of acquiring the medical image information. The predominant direction of movement is in particular parallel to an axis relative to which the distance of the medical imaging apparatus (in particular the source of imaging radiation) remains constant during acquisition of the medical image information. This axis is also termed movement axis and is in particular substantially parallel to a caudo-cranial axis of the patient's body and further particularly, is identical to the caudo-cranial axis. The predominant direction of movement is preferably acquired based on determining an orientation of the movement axis. This orientation is determined in particular relative to (further particularly, in) the navigation coordinate system.

Preferably, the predominant direction of movement is alternatively or additionally acquired based on determining a translational component of the movement of the medical imaging apparatus between its position at the beginning and its position at the end of acquiring the medical image information.

The predominant direction of movement is preferably determined based on normalizing the distance described by the difference in the translational component of the movement of the medical imaging apparatus. Therein, it is assumed that the movement of the medical imaging apparatus leads to a change in only one coordinate component of the position of the medical imaging apparatus. It is assumed that the medical imaging apparatus may be translated in only the direction defined by that coordinate component and that it cannot be translated in the other two spatial directions which are in particular perpendicular to the predominant direction of movement. However, in particular in the case of the movable part of the medical imaging apparatus comprising the gantry of a CT or MR scanner, it may not be excluded that the movable part of the medical imaging apparatus may be rotated and therefore comprises at least one further degree of freedom which is non-zero. However, it is assumed that, during acquisition of the medical image information, the medical imaging apparatus (in particular a gantry of a CT or MR scanner) is moved in only one degree of freedom, namely that it is translated along the predominant direction of movement. In particular, the imaging radiation source used for generating the medical image information is not rotated (in particular not rotated around the predominant movement direction and/or the axis of translation) during the movement.

Preferably, information about the position of a pointer means in the predominant direction of movement is acquired. For example, the pointer is a pointer instrument which is pointed at the anatomical structure. A pointer instrument is in particular a rod which comprises one or more—advantageously two—in particular retroreflective markers fastened to it and which can be used to measure individual coordinates, in particular spatial coordinates (i.e. three-dimensional coordinates), on a structure such as a part of the patient's body in particular based on detection of the markers with a medical navigation system. The markers preferably have a predetermined and further preferably fixed spatial relationship (i.e. at least one of position and/or orientation) relative to the rod and relative to each other. Alternatively, the pointer is embodied by an optical pointing means such as a laser emitter which emits a laser beam onto the patient's body such that it points towards the anatomical structure which can be checked visually by user interaction. The laser emitter preferably has a known position in the navigation coordinate system (in particular a known distance from a structure having a predetermined position such as the medical imaging apparatus in its start position or a device for placing the patient's body such as a bed of a CT scanner) and the direction in which it is pointing (i.e. the spatial relationship between the anatomical structure and the laser emitter) is acquired by a detection unit embodied by orientation sensors operatively coupled to the laser emitter for determining its orientation. In such a case, preferably the position of the anatomical structure is known in two coordinate directions of the navigation coordinate system, and the third coordinate direction is predetermined as being at least substantially parallel to the predominant direction of movement. For example, the patient's body is placed on a table having a predetermined spatial relationship relative to the medical imaging apparatus and the medical imaging apparatus can be translated only in for example the longitudinal direction of the table. Thereby, the position of the patient's body lying on the table is predetermined and preferably fixed in two spatial directions. The pointer then serves to determine a position of an anatomical structure contained in the patient's body in the third spatial direction.

According to a further preferred embodiment, the position of the pointer is determined relative to a position of the medical imaging apparatus which it takes at the end or after acquiring the medical image information. For example, the medical imaging apparatus may be moved to an in particular predetermined position after acquiring the medical image information so as not to hinder access to the patient's body. This supports easy transformation of the position which is identified by the pointer (i.e. the position towards the pointer is pointing which is described by in particular at least one coordinate component of the position of the anatomical structure) into the position of image features in the medical image information representing the anatomical structure. This is because the medical image information comprises in particular a sequence of medical images which are taken along the predominant direction of movement of the medical imaging apparatus, i.e. in a linear direction. Preferably, a distance is determined between the position in the predominant direction of movement (i.e. in the coordinate component describing that direction) identified by the pointer and the position which the medical imaging apparatus takes at the same point in time (in particular the coordinate component of that position which lies in the predominant direction of movement). This distance therefore corresponds to a one-dimensional distance since it suffices to describes this distance in one component of the navigation coordinate system.

In particular on the basis of the information about the position of the medical imaging apparatus at the beginning of acquiring the medical image information and at the end of acquiring the medical image information and on the basis of the information about the position of the pointer means and on the basis of the imaging information, information about a transformation between the position in the medical image of an image feature representing the anatomical structure (in the medical image information) and the position of the anatomical structure in the navigation coordinate system (in particular in the predominant direction of movement) is determined. The information about the transformation for example describes a transformation between the amount of pixels contained in the medical image information in the predominant direction of movement and the respective distance travelled by the medical imaging apparatus during the movement. In particular, each pixel position along the predominant direction of movement is transformed into (i.e. associated with) a position of the medical imaging apparatus in the predominant direction of movement in particular during acquisition of the medical image information. The transformation therefore is in particular a coordinate transformation, in particular a mapping between the coordinate system used to determine positions of image features in the medical image information and the coordinate system in which the position of the anatomical structure is described (which is in particular the navigation coordinate system). The transformation advantageously considers only one dimension, i.e. maps only one coordinate component of each coordinate system. This component is in particular the component corresponding to the predominant direction of movement. For example, the predominant direction of movement is determined as direction represented by the coordinate component (of the translation of the medical imaging apparatus in particular the corresponding axis of the navigation coordinate system) in which the largest difference occurs between the position of the medical imaging apparatus at the beginning of acquiring the medical image information and its position at the end of acquiring the medical image information. The predominant direction of movement corresponds to the predominant direction along which the medical image information renders e.g. the image representation of parts of the patient's body in a preferred constant time increment per set (e. g. column or row) of image units (e. g. pixels or voxels). This time increment corresponds in particular to the time travelled by the medical imaging apparatus during its translation. The predominant direction along which the medical image information renders e.g. the image representation of parts of the patient's body is also called predominant image direction.

The transformation serves to determine information about the position of an image feature representing a real anatomical structure in the medical image information based on predetermined (in particular known) information about the position of the real anatomical structure. The transformation also serves to determine information about the position of a real anatomical structure based on predetermined (in particular known) information about the position of an image feature representing the real anatomical structure in the medical image information.

The transformation can be expressed by the following equation:

$$z(\text{selected}) = [n_s/(n_x-1)] \cdot [z(\text{end}) - z(\text{start})] \quad (1)$$

where:
- z(selected) is the value of the coordinate component (e.g. the z-component) of the position of the marker means in the predominant direction of movement (represented by for example the z-direction);
- $n_s$ is the number of the set of image units (e.g. the column number of the column of pixels) representing the image information taken at the point in time at which the z-position of the medical imaging apparatus is z=z(selected);
- $n_x$ is the total number of sets of image units along the predominant image direction, e. g the total number of pixel columns;
- z(start) is the value of the coordinate component (e.g. z-component) of the position of the medical imaging apparatus in the predominant direction of movement which it has at the beginning of taking the medical image information;
- z(end) is the value of the coordinate component (e.g. z-component) of the position of the medical imaging apparatus in the predominant direction of movement which it has at the end of taking the medical image information.

The inventive method therefore preferably comprises a step of determining, based on the information about the position of the medical imaging apparatus at the beginning and at the end of the acquiring the medical image information and based on the information about the position of the pointer, the position in the medical image of an image feature representing the anatomical structure. In particular, it is then possible to identify the anatomical structure in the medical image information lying at the position identified by the pointer. Such identification is supported for example by issuing a visual and/or audible indication to a user. For example, the image feature representing the respective anatomical structure in the medical image information is highlighted on a display device such as a monitor operatively coupled to the computer of the medical navigation system. Alternatively, or additionally, the user may be supplied with an audio signal issued from for example a loudspeaker associated with the computer of the navigation system if the pointer identifies a position at which an anatomical feature corresponding to a predetermined image feature in the medical image information lies. Thereby, medical personnel may also identify an anatomical structure in the real world based on selecting a specific image feature by e.g. scanning the patient's with the pointer means body until the information about the position of the pointer means indicates that it has the same value in the component along the predetermined direction of movement as the as the value describing the position of the respective image feature in the predominant image direction.

In all coordinate components of the navigation coordinate system, the position of the pointer means (and the anatomical structure) at which its z-component is z(selected) may therefore by determined based on the following equation, assuming that its position is determined relative to the position of the medical imaging apparatus at the end of acquiring the medical image information:

$$\text{pos(selected)} = \text{pos(end)} + \{[z(\text{selected}) - z(\text{end})]/[z(\text{end}) - z(\text{start})]\} \cdot \{[\text{pos(end)} - \text{pos(start)}]/[\|\text{pos(end)} - \text{pos(start)}\|]\} \quad (2)$$

where:
- pos(selected) is the position of the marker means at which its coordinate component in the predominant direction of movement is z(selected);
- pos(start) is the position of the medical imaging apparatus which it has at the beginning of taking the medical image information;
- pos(end) is the position of the medical imaging apparatus which it has at the end of taking the medical image information; ‖ ‖ is a norm operator which is applicable to the navigation coordinate system. The norm operator may be a norm operator in Euclidean space such as an $L_n$ norm, where n denotes the dimensionality of the navigation coordinate system. Preferably, n=3.

The invention also relates to a program which, when running on a computer or when loaded on a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program in particular the aforementioned program, which in particular comprises code means which are adapted to perform any or all of the method steps described herein. The computer can also be a cloud computer.

Furthermore, the invention also relates to a medical navigation system comprising the aforementioned computer, a display device for displaying the medical image information (such as a monitor which may be movable, for example handheld—e.g. the monitor of a mobile device such as a mobile phone, or stationary in particular relative to the navigation coordinate system), and a detection unit (e.g. a camera) for detecting the positions of the medical imaging apparatus and the pointer means, respectively.

In particular, the invention does not involve, in particular it does not comprise or encompass, an invasive step which would represent a substantial physical interference with the body requiring professional medical expertise to be carried out and entailing a substantial health risk even when carried out with the required professional care and expertise. In particular, the invention does not comprise a step of placing the medical implant in position for fastening it to the anatomical structure or a step of fastening the medical implant to the anatomical structure or a step of preparing the anatomical structure for being fastened to the medical implant. More particularly, the invention does not involve (in particular comprise or encompass) any surgical or therapeutic activity. Rather, the invention preferably comprises a step of orienting a pointing means towards an anatomical structure which to do so does not need to have been uncovered by way of surgery. For at least this reason, no surgical or therapeutic activity (in particular no surgical or therapeutic step) is necessitated or implied by carrying out the invention.

DEFINITIONS

Terminology used in the present disclosure is described in the following, and the following description also forms part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument).

It is the function of a marker to be detected by a detection unit (for example, a camera or an ultrasound receiver or analytical devices such as CT or MRI) in such a way that information about its spatial position (i.e. its spatial location and/or alignment) can be acquired. The detection unit is in particular part of a navigation system. The markers can be active markers. An active marker can for example emit electromagnetic radiation and/or waves which can be in the infrared, visible and/or ultraviolet spectral range. The marker can also however be passive, i.e. can for example reflect electromagnetic radiation in the infrared, visible and/or ultraviolet spectral range or can block x-ray radiation (i.e. it can be radioopaque). To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is in particular known to a navigation system and is for example stored in a computer of the navigation system.

A navigation system, in particular a medical navigation system, is understood to mean a system which preferably comprises: at least one marker device; a transmitter which emits electromagnetic waves (e.g. in the infrared wavelength range) and/or electromagnetic radiation and/or ultrasound waves; a receiver (e.g the detection unit) which receives electromagnetic waves and/or radiation and/or ultrasound waves; and an electronic data processing device which is connected to the receiver and/or the transmitter, wherein the data processing device (for example, a computer) in particular comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

In the field of medicine, medical imaging methods are used to generate medical image data (for example, two-dimensional or three-dimensional image data) comprising medical image information, e.g. image representations of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, in particular volumetric CBCT), x-ray tomography, magnetic resonance tomography (MRT or MRI), conventional x-ray, sonography and/or ultrasound examinations, and positron emission tomography. Analytical devices in particular are used to generate the medical image data in apparatus-based imaging methods. The medical imaging methods are in particular used for medical diagnostics, to analyse the anatomical body in order to generate images which are described by the image data. Medical imaging methods are also in particular used to detect pathological changes in the human body.

The method in accordance with the invention is in particular a data processing method. The data processing method is preferably performed using technical means, in particular a computer. The data processing method is in particular constituted to be executed by or on the computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. The data is embodied by for example magnetic or optical information stored in magnetic or optical data storage media. The data comprises information content which describes certain in particular physical quantities as in particular disclosed herein.

DESCRIPTION OF THE FIGURES

In the following, the invention is described with reference to the Figures which represent preferred embodiments of the invention without limiting the invention to the specific features shown in the Figures.

FIG. 1a shows a set-up of a CT scanner and a patient placed on a bed as well as a medical navigation system for tracking the position of the CT scanner and a pointer instrument;

FIG. 1b shows the anatomical structure depicted in medical image acquired by the CT scanner; and FIGS. 2a and 2b show equations on the basis of which the position of the anatomical structure in the medical image can be determined.

According to FIG. 1a, a patient's body 2 comprising an anatomical structure embodied by a vertebra 3 is placed on a table 16 having a predetermined spatial relationship relative to the gantry 1 of the CT scanner, wherein the gantry represents the medical imaging apparatus in the sense of this disclosure. A marker device 4 comprising three retroreflective markers 15 is fixedly attached to the gantry 1. Furthermore, a medical navigation system 10 comprising a computer which includes a microprocessor 5, a volatile memory 6 and a non-volatile memory 7 and is operatively coupled to a monitor 9 serving as a display device of the medical navigation system and a stereotactic camera 8 which is sensitive in the infrared wavelength range embodying the detection unit of the medical navigation system 10, is positioned such that the marker spheres 15 are in the field of view of the camera 8.

A medical image, in particular an overview image (also called scout view), of the patient's spine is generated by traveling the gantry 1 to take a series of medical images along the caudo-cranial axis of the spine. Such an overview image desirably covers sufficiently many vertebrae to allow for a correct identification of the level of the spine to be treated for example in later medical procedures such as a surgical procedure. It is noted that no such surgical procedure is part of the inventive method. In order to take the overview image of the spine, the gantry is moved along the z-direction of the navigation coordinate system 17 representing the predominant direction of movement and the X-ray source in the gantry is preferably kept at a constant rotational position relative to the caudo-cranial axis of the patient's body 2 (in particular at y=0 in the navigation coordinate system 17). The gantry 1 is moved from its starting position pos(start) which is characterized by a positional component z(start) in the z-direction and which the gantry 1 takes at the beginning of acquiring the medical image information. The gantry 1 is moved until it takes its end position pos(end) which is characterized by a positional component z(end) in the z-direction and which the gantry 1 takes at the end of acquiring the medical image information. The position of the gantry 1 is tracked at least at the beginning and the end of acquiring the medical image information by the navigation system 10 which detects the positions of the marker spheres 15.

Between the point in time at which the gantry 1 has its starting position and the point of time at which the gantry has its end position, the camera 8 preferably does not move relative to the navigation reference system 17. In particular, the camera 8 does not move relative to the start position of the gantry 1.

The gantry 1 is operatively coupled for example by a data communication line 18 to the computer 5, 6, 7 of the navigation system 10 in order to transmit signals representing the medical image information to the computer 5, 6, 7 for further processing. The computer 5, 6, 7 processes the signals in order to generate a medical image 11 representing the desired overview and is shown in FIG. 1b. The medical image 11 has a length of $n=n_x$ pixels which are normalized to each represent a specific distance travelled by the gantry 1 in the z-direction (equaling in particular to a distance of $\Delta z = z(end) - z(start)$). The information about this normalization corresponds to the imaging information and is determined based on the aforementioned positional tracking of the gantry 1, time information about the times at which the gantry 1 has its starting and end position, respectively, and based on predetermined or measured (online) information about e.g. the imaging frequency of the CT scanner. A user such as medical personnel orients a pointer means embodied by a pointer instrument 12 (to which marker devices 13 having each at least one marker sphere 15 are fixedly attached) such that the pointer instrument 12 points at the position of the vertebra 3 which can be for example visibly or tactilely determined by the user. The user wishes to have information which of the vertebrae 3 shown in the medical image 11 corresponds to the vertebra 3 at which he is pointing the pointer instrument 12. In this example, the pointer instrument 12 points at a position z(selected) representing the position of the vertebra 3 in the z-direction of the navigation reference system 17. The predominant direction of movement of the gantry 1 is represented by the z-direction of the navigation reference system 17 and in this case is parallel to the longitudinal axis of the table 16 and the caudo-cranial axis of the patient's body 2. If the pointer instrument 12 identifies a specific selected position pos (selected) having a positional component in the z-direction of z(selected) by pointing at pos(selected), the positional component z(selected) in the z-direction can be determined by determining the distance between the marker spheres 15 on the marker devices 13 and on the marker device 4, respectively. In the example of the Figures, such determination is effected by optical detection of the marker spheres 15 with the camera 8. Thereby, an easy and reliable way of determining the z-component of the position of the vertebra 3 is provided. It is in particular advantageous that the user does not need to point the pointer instrument 12 at a specific x- and y-position in order to determine the position of the vertebra 3. It will be enough to point the pointer instrument 12 at the desired z-position of the vertebra 3 which makes correct use of the pointer instrument 12 within the inventive method less cumbersome for the user. The x- and y-components of the position of the vertebra 3 are predetermined by the positioning of the patient on the table 16. In particular, the table 16 and/or or the patient's body 2 (in particular the anatomical structure embodied by the vertebra 3) do not move relative to the navigation reference system 17 during the whole of the execution of the inventive method.

The position z(selected) is translated into a position $n=n_s$ designating the position of the image feature representing the vertebra 3 along the length dimension of the medical image 11 based on equation (1) which is also shown in FIG. 2a. The length dimension of the medical image 11 is the dimension along which the pixels accounted in terms of the variable n in the example shown in the Figures, z(selected) is determined based on determining the position of the pointer instrument 12 relative to the marker device 4 attached to the gantry 1 at the end of taking the medical image information. FIG. 2b shows equation (2), based on which the three-dimensional position pos(selected) identified by the pointer device 12 and representing the three-dimensional position of the vertebra 3 is then determined relative to the end position pos(end) of the gantry 1. Determining the position of the pointer instrument 12 relative to the position of the gantry 1 allows in particular to move the camera 8 for example relative to the navigation reference system 17 after acquisition of the medical image information (in particular acquisition of the overview image 11) has been completed. If the gantry is moved to a position differing from pos(end) after the end of acquiring the medical image information, a corresponding subtractive or additive term has to be introduced into equation (2) if the position of the pointer instrument is to be determined relative to the position of the gantry 1 and/or the position of the marker device 4.

An exemplary application of the present invention is described as follows: The user wishes to identify a specific vertebra 3 highlighted in the medical image 11 (as shown in FIG. 1b by a dotted square frame) in the display on the monitor 9. To this end, he points the pointer instrument 12 at the patient's spine and moves it along the longitudinal axis of the spine (in particular in the caudo-cranial direction i.e. in the example shown in the Figures along the predominant direction of movement in the z-direction) until the navigation system 10 determines that the pointer instrument 12 is pointing at the vertebra 3 highlighted in the medical image 11. The user can then be supplied for example with an audio signal issued by a loudspeaker operatively coupled to the computer (5, 6, 7) of the navigation system 10. The user will then for example know which of the patient's vertebrae 3 is to be targeted by the following medical procedure.

Alternatively, the user may wish to identify a specific vertebra 3 in the medical image 11. To this end, he points the pointer instrument 12 at z-position of the specific vertebra 3 in the patient's body 2 and by acquiring information about the position identified by the pointer instrument 12 and by translating the real-world coordinates in the navigation coordinate system 17 into pixel coordinates in the medical image 11, the corresponding image representation of the vertebra 3 can be identified and highlighted as shown in for example FIG. 1*b* by a dotted square frame.

An advantage of the present invention is that, for example, the inventive method can also be carried out with a gantry 1 which is tilted along for example a y-direction while taking the overview image. However, it is preferred that the distance of the marker spheres 15 attached to the marker device 4 (and the gantry 1) to the table 16 (the longitudinal extent of which being parallel to the z-direction) remains constant while the overview image is taken.

The invention claimed is:

1. A computer-implemented method of relating a position of an anatomical structure and a position of an image feature representing the anatomical structure in a medical image, the method comprising executing, on a processor of a computer, steps of:
   a) acquiring, at the processor, information about a position of a medical imaging apparatus at a beginning and at an end of acquiring medical image information describing a medical image of at least a part of a patient's body comprising the anatomical structure, wherein the medical imaging apparatus is moved while it is used for acquiring the medical image information;
   b) acquiring, at the processor, imaging information about a relationship between the movement of the medical imaging apparatus and the acquisition of the medical image information;
   c) acquiring, at the processor and based on the position of the medical imaging apparatus at the beginning and at the end of acquiring the medical image information, information about a predominant direction of movement of the medical imaging apparatus;
   d) acquiring, at the processor, information about the position of a pointer means in the predominant direction of movement;
   e) determining, by the processor and based on the information about the position of the medical imaging apparatus at the beginning and at the end of acquiring the medical image information and based on the information about the position of the pointer means and based on the imaging information, information about a transformation between a position in the medical image of an image feature representing the anatomical structure and a position of the anatomical structure in a navigation reference system.

2. The method according to claim 1, wherein the predominant direction of movement is acquired, at the processor, based on determining an axis relative to which a distance of the medical imaging apparatus remains constant during acquisition of the medical image information.

3. The method according to claim 2, wherein the predominant direction of movement is substantially parallel to a caudo-cranial axis of the patient's body.

4. The method according to claim 1, wherein determining the transformation includes determining, by the processor, information about the position of an image feature representing the anatomical structure in the medical image based on information about the position of the anatomical structure in the predominant direction of movement.

5. The method according to claim 1, wherein determining the transformation includes determining, by the processor, the position of the anatomical structure in the predominant direction of movement based on information about the position of an image feature representing the anatomical structure in the medical image.

6. The method according to claim 1, wherein the predominant direction of movement is acquired based on determining, by the processor, information about a translational component of the movement of the medical imaging apparatus between its position at the beginning and its position at the end of acquiring the medical image information.

7. The method according to claim 1, wherein the information about the position of the pointer means describes a position of the pointer which is determined relative to a position of the medical imaging apparatus at the end or after acquiring the medical image information.

8. The method according to claim 7, wherein the information about the position of the medical imaging apparatus and the information about the position of the pointer means are determined, by the processor, based on information generated by detecting marker devices having a predetermined spatial relationship relative to the medical imaging apparatus and the pointer, respectively.

9. The method according to claim 8, wherein the marker devices comprise retroreflective markers.

10. The method according to claim 1, wherein the position of the anatomical structure is indicated by at least one of a visual and an audible signal.

11. The method according to claim 1, wherein the medical imaging apparatus is a CT scanner or an MR scanner.

12. The method according to claim 1, wherein the medical imaging apparatus does not rest relative to a coordinate system in which the positions acquired and determined in the method are defined.

13. The method according to claim 1, wherein the pointer means is a pointer instrument or an optical pointing means.

14. A non-transitory computer-readable program storage medium storing a computer program which, when executed on a processor of a computer or loaded into a memory of the computer, causes the computer to execute a computer-implemented method of relating a position of an anatomical structure and a position of an image feature representing the anatomical structure in a medical image, the method comprising executing, on the processor, steps of:
   a) acquiring, at the processor, information about a position of a medical imaging apparatus at a beginning and at an end of acquiring medical image information describing a medical image of at least a part of a patient's body comprising the anatomical structure, wherein the medical imaging apparatus is moved while it is used for acquiring the medical image information;
   b) acquiring, at the processor, imaging information about a relationship between the movement of the medical imaging apparatus and the acquisition of the medical image information;
   c) acquiring, at the processor and based on the position of the medical imaging apparatus at the beginning and at the end of acquiring the medical image information, information about a predominant direction of movement of the medical imaging apparatus;
   d) acquiring, at the processor, information about the position of a pointer means in the predominant direction of movement;

e) determining, by the processor and based on the information about the position of the medical imaging apparatus at the beginning and at the end of acquiring the medical image information and based on the information about the position of the pointer means and based on the imaging information, information about a transformation between a position in the medical image of an image feature representing the anatomical structure and a position of the anatomical structure in a navigation reference system.

15. A computer comprising the program storage medium according to claim 14.

16. A medical navigation system, comprising:
a computer comprising a processor, the processor being configured to execute a computer-implemented method of relating a position of an anatomical structure and a position of an image feature representing the anatomical structure in a medical image, the method comprising executing, on the processor, steps of:
a) acquiring, at the processor, information about a position of a medical imaging apparatus at a beginning and at an end of acquiring medical image information describing a medical image of at least a part of a patient's body comprising the anatomical structure, wherein the medical imaging apparatus is moved while it is used for acquiring the medical image information;
b) acquiring, at the processor, imaging information about a relationship between the movement of the medical imaging apparatus and the acquisition of the medical image information;
c) acquiring, at the processor, and based on the position of the medical imaging apparatus at the beginning and at the end of acquiring the medical image information, information about a predominant direction of movement of the medical imaging apparatus;
d) acquiring, at the processor, information about the position of a pointer means in the predominant direction of movement;
e) determining, by the processor and based on the information about the position of the medical imaging apparatus at the beginning and at the end of acquiring the medical image information and based on the information about the position of the pointer means and based on the imaging information, information about a transformation between a position in the medical image of an image feature representing the anatomical structure and a position of the anatomical structure in a navigation reference system;
a display device for displaying the medical image information; and
a detection unit for detecting the positions of the medical imaging apparatus and the pointer means.

* * * * *